(12) United States Patent
Iwanaga et al.

(10) Patent No.: US 7,902,741 B2
(45) Date of Patent: Mar. 8, 2011

(54) FLUORESCENT COMPLEX AND LIGHTING SYSTEM USING THE SAME

(75) Inventors: Hiroki Iwanaga, Yokohama (JP); Akio Amano, Kawasaki (JP); Fumihiko Aiga, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 445 days.

(21) Appl. No.: 11/471,011

(22) Filed: Jun. 20, 2006

(65) Prior Publication Data

US 2007/0007884 A1 Jan. 11, 2007

(30) Foreign Application Priority Data

Jun. 21, 2005 (JP) .................... 2005-180421

(51) Int. Cl.
*H01J 1/62* (2006.01)
*C07F 9/6568* (2006.01)

(52) U.S. Cl. ........................................ 313/504; 568/12

(58) Field of Classification Search .................. 313/504; 568/12

See application file for complete search history.

(56) References Cited

U.S. PATENT DOCUMENTS

| 6,656,608 | B1 * | 12/2003 | Kita et al. ............ 428/690 |
| 2004/0265631 | A1 * | 12/2004 | Iwanaga et al. .......... 428/690 |

FOREIGN PATENT DOCUMENTS

| JP | 05-320093 | 12/1993 |
| JP | 06-184151 | 7/1994 |
| JP | 11-005837 | 1/1999 |
| JP | 2001-143869 | 5/2001 |
| JP | 2003-509434 | 3/2003 |
| JP | 2003-262936 | 9/2003 |
| JP | 2005-15564 | 1/2005 |
| JP | 2005-44930 | 2/2005 |
| WO | 01/19838 | 3/2001 |

OTHER PUBLICATIONS

Vincens et al. "Synthese de tetra oxydes de phosphine macrocycliques a partit des bisphophoniums bis oxydes de phosphine correspondants" Tetrahedron, 1991, vol. 47, No. 3, pp. 403-410.*

Vincens, et al., Tetrahedron, Synthese De Tetra De Phosphine Macrocycliques A Partir Des Bisphosphoniums Bis Oxydes De Phosphine Correspondants, vol. 47, No. 3, pp. 403-410, 1991.

Barakat, et al., Journal of Chemical Society, Oxidation of Organic Compounds by Solid Manganese Dioxide, pp. 4685-4687, 1956.

Mukaiyama, et al., Journal of Organic Chemistry, Oxidation of Phosphites and Phosphines via Quaternary Phosphonium Salts. pp. 101-105, Jan. 1965.

Japanese Office Action for 2005-180421 mailed on Oct. 23, 2009.

Koordinatsionnaya Khimiya, 1990, vol. 16, No. 12, pp. 1688-1692.

Izvestiya Akademii Nauk SSSR, Seriya Khimicheskaya, 1986, No. 4, pp. 810-815.

Synthesis and Reactivity in Inorganic and Metal-Organic Chemistry, 1999, vol. 29, No. 7, pp. 1183-1198.

Inorganic Chemistry, 2002, 41(4), pp. 685-692.

Journal of Chemical Society, Perkin Transactions 2, 2001, (11), pp. 2219-2225.

Tetrahedron, 2001, 57(26), pp. 5557-5563.

* cited by examiner

*Primary Examiner* — Joseph R Kosack

(74) *Attorney, Agent, or Firm* — Turocy & Watson, LLP

(57) ABSTRACT

Disclosed are a fluorescent complex comprising a rare earth atom and a ligand having a structure comprising a plurality of coordinating groups bonded to each other in a ring form, and a lighting system and a flashlight device using the same. This fluorescent complex can realize high-intensity fluorescence and a prolonged service life and gives a sharp fluorescence spectrum.

7 Claims, 2 Drawing Sheets

FLUORESCENT COMPLEX AND LIGHTING SYSTEM USING THE SAME

CROSS-REFERENCE TO RELATED APPLICATIONS

This application is based upon and claims the benefit of priority from the prior Japanese Patent Applications No. 180421/2005, filed on Jun. 21, 2005; the entire contents of which are incorporated herein by reference.

BACKGROUND OF THE INVENTION

1. Field of the Invention

The present invention relates to a fluorescent complex and a lighting system possessing a high level of luminosity and a prolonged service life.

2. Background Art

In recent years, the luminosity and service life of LED elements have been significantly improved, and a wide range market development including illumination applications is under way.

For LED elements using inorganic fluorescent substances which are currently mainly adopted, the luminescence efficiency is being significantly improved. In particular, it is said that the luminescence efficiently of white LEDs would excel that of fluorescent lamps in the future. When LEDs are used in lighting systems, in many applications, the LEDs should be excellent in luminescence efficiency, as well as in color rendering properties. The present situation, however, is that LEDs using only inorganic fluorescent substances cannot satisfy all of these property requirements without difficulties.

The concept that organic fluorescent substances are used in LEDs is already known. At the present time, however, LEDs using organic fluorescent substances as the fluorescent substance have not been put to practical use in illumination applications due to the presence of the following problems.

1) In particular, when near ultraviolet LEDs, which are currently being mainly adopted, are used as a light source and organic fluorescent substances are used in LEDs using luminescent materials for R, G, and B, a deterioration in organic compounds by ultraviolet light is significant, because organic compounds are generally weak against ultraviolet light.

2) Since organic fluorescent substances sometimes causes a variation in a fluorescence spectrum depending upon its concentration, the regulation of the spectrum is difficult. Further, the fluorescence intensity depends upon the concentration, and, thus, concentration quenching disadvantageously takes place in a high concentration region.

3) The fluorescence spectrum sometimes disadvantageously varies depending upon the type of polymer dispersed in the organic fluorescent substance.

In general, the fluorescent substance formed of a rare earth complex has the following advantages over conventional organic fluorescent substances.

1) The luminescence wavelength is characteristic of rare earthes and thus is less likely to be influenced by the coloring matter and the type of polymer to be dispersed, and, thus, the fluorescence spectrum is stable.

2) Although the ligand is an organic compound, upon the excitation of the ligand through the absorption of light, the state is returned to the ground state by energy transfer to the central element. Accordingly, the opportunity for causing an irreversible chemical change from the excited state is reduced, and, thus, durability against ultraviolet light can be expected.

However, a further improvement in luminosity and service life is required for developing general illumination markets. Stability against a photochemical reaction of the ligand per se may be mentioned as a property which greatly affects the durability. Fluorescent substances exposed to light from LED are exposed to severe conditions such as strong heat and light and thus are likely to be deteriorated radically (oxidatively). A chemical change in ligand lowers a coordinative ability, resulting in the removal of the ligand. In some cases, this often deteriorates fluorescence intensity, and the altered ligand is causative of deactivation.

On the other hand, in order to realize high luminosity, the solubility or dispersibility of the fluorescent complex in the resin should be large. When the fluorescent substance is present as particles in the resin due to low solubility or dispersibility, light scattering occurs and makes it impossible to provide satisfactory luminosity.

The polymer in which the rare earth complex is dissolved significantly affects the luminosity of the LED element. Specifically, rare earth complexes, particularly europium complexes, when C—H bond or O—H bond is present around ions, cause quenching as a result of vibrational deactivation. That is, when C—H bond or O—H bond is present in the polymer in which the rare earth complex is dissolved, there is a tendency that the fluorescence intensity is disadvantageously attenuated. Eliminating the whole of the above bonds from the polymer, however, is practically impossible.

For example, rare earth complexes to which a crown ether has been coordinated are also known (see, U.S. Pat. No. 6,656,608). In such conventional complexes, oxygen constituting the ether group is a coordinating group. Since, however, the coordinating ability is relatively low, there is room for improvement in stability as the complex. Further, regarding complexes described in U.S. Pat. No. 6,656,608 which have a crown ether as a ligand, there is also room for improvement in the effect of shielding against C—H bond or O—H bond present near the complex when the complex is dissolved in the resin or the like.

BRIEF SUMMARY OF THE INVENTION

The present invention has been made under the above circumstances, and an object of the present invention is to realize a lighting system having a high level of luminosity and a prolonged service life that are satisfactory for lighting system applications.

The present inventors have made intensive and extensive studies with a view to attaining the above object and, as a result, have found that a high level of luminosity and a high level of durability can be realized by using a fluorescent complex with a specific ligand introduced thereinto. This has led to the completion of the present invention. Thus, according to the embodiment, there is provided a fluorescent complex comprising a rare earth atom and at least one cyclic multidentate ligand coordinated to the rare earth atom, said cyclic multidentate ligand having a structure in which a plurality of coordinating groups are bonded to each other in a ring form.

According to another aspect of the embodiment, there is provided a lighting system comprising a light emitting element having a light emitting face and a fluorescent layer disposed on or above said light emitting element on the side of the light emitting face, said fluorescent layer comprising the above fluorescent complex.

According to a further aspect of the embodiment, there are provided a camera and a cellular phone with a camera, the camera comprising a lighting system comprising a light emitting element having a light emitting face and a fluorescent layer disposed on or above said light emitting element on the side of the light emitting face, said fluorescent layer comprising the above fluorescent complex.

The fluorescent complex according to the embodiment is a novel compound that can realize high-intensity fluorescence and prolonged service life, because, when the fluorescent complex is dispersed or dissolved in resins or the like, the rare earth atom located at the center is shielded against C—H bond or O—H bond causative of vibrational deactivation by virtue of a relatively low-molecular weight cyclic multidentate ligand encompassing the fluorescent complex. Further, the fluorescent spectrum of the fluorescent complex according to the embodiment is sharp. When the fluorescent complex according to the embodiment is used in a flashlight device in a cellular phone with a camera, a sharp personal image can be photographed. Further, when the fluorescent complex according to the embodiment is used in lighting equipment, a relaxation lighting space close to natural light can be realized.

DETAILED DESCRIPTION OF THE INVENTION

Figure 1:
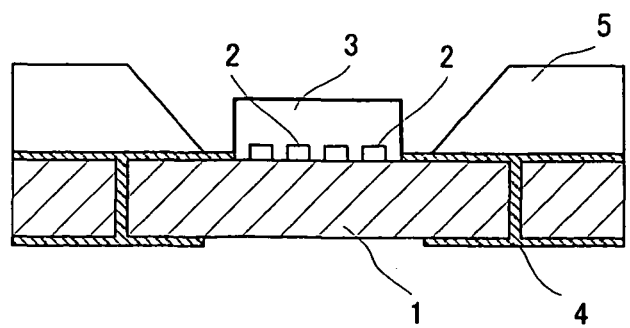
FIG. 1 is a cross-sectional view of an LED flashlight device using the fluorescent complex according to one embodiment.

The fluorescent complex according to on embodiment of the present invention comprises a rare earth complex comprising a rare earth atom and at least one cyclic multidentate ligand coordinated to the rare earth atom. The cyclic multidentate ligand has a structure comprising a plurality of coordinating groups bonded to each other in a ring form. The coordinating group refers to an atomic group or an atom having a lone electron pair which can be coordinately bonded to the rare earth atom. More specifically, an atomic group containing an O atom having a lone electron pair, a nitrogen atom having a lone electron pair, and a selenium atom having a lone electron pair, for example, P=O, S=O, O=S=O, and C=O.

The cyclic multidentate ligand contained in the fluorescent complex according to one embodiment of the present invention has a structure comprising two or more coordinating groups bonded to each other in a ring form. The bonding group for bonding the coordinating groups is not particularly limited. The bonding group, however, is generally a carbon chain having a straight chain or branched chain structure. This bonding group optionally contains an ether bond or optionally contains a substituent such as a hydroxyl, carboxyl, sulfonic acid, or amino group.

The cyclic multidentate ligand is preferably represented by general formula (A)

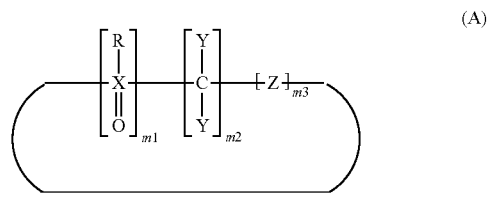

Wherein:

X represents an atom selected from the group consisting of phosphorus, sulfur, and carbon, and, when a plurality of X's are present in the molecule, they may be the same or different, R represents a substituent selected from the group consisting of substituted or unsubstituted straight chain or branched chain alkyl or alkoxy having 20 or less carbon atoms, phenyl, biphenyl, naphthyl and a heterocyclic group when X bonded to R is phosphorous; R is absent when X bonded to R is a carbon atom; R is absent or represents oxygen bonded to a sulfur atom through a double bond when X bonded to R is the sulfur atom; and when a plurality of R's are present in the molecule, they may be the same or different, Y represents hydrogen or an alkyl or alkoxy having 20 or less carbon atoms; Y's in the molecule may be the same or different; and Y may be bonded to another Y in the molecule through a carbon chain optionally containing oxygen to form a crosslinked ring structure, Z represents a divalent group selected from the group consisting of —O—, —NY$^a$—, —S—, and —Se— wherein Y$^a$ represents a substituent selected from the group consisting of substituted or unsubstituted straight or branched alkyl and alkoxy having 20 or less carbon atoms, phenyl, biphenyl, naphthyl and a heterocyclic group; Y$^a$ may be bonded to another Y or Y$^a$ in the molecule through a carbon chain optionally containing oxygen to form a crosslinked ring structure; and when a plurality of Z's are present in the molecule, they may be the same or different;

m1 and m3 are independently an integer including 0 (zero), m1+m3 being 2 or more, m2 is an integer of m1+m3 or more, and wherein:

—X(=O)R—, —CY$_2$—, and —Z— in the formula are arranged randomly and are bonded to one another in a ring form.

—X(=O)R—, —CY$_2$—, and —Z—, which are bonding units, are bonded randomly to each other rather than the formation of blocks of the units, or alternatively may be bonded attributively.

In this formula, X=O or Z functions as the coordinating group in the cyclic multidentate ligand. The cyclic multidentate ligand is preferably that X represents a phosphorous, sulfur or carbon atom, or —NY$^a$— or —Se—. The coordinating group is particularly preferably P=O, S=O, O=S=O, or C=O, most preferably P=O, S=O, or O=S=O. In other words, most preferably, m1 is 2 or more. In this case, m3 may be 0 (zero).

These coordinating groups are bonded to each other in a ring form optionally through a linking group —CY$_2$—. The total number of coordinating groups is 2 or more, preferably 4.

In the fluorescent complex according to the embodiment, the above cyclic multidentate ligand is coordinated to the rare earth atom. Preferably, however, the ring formed by the plurality of coordinating groups is not excessively large. For the above reason, the following (A1), (A2) and (A3), which will be described in more detail, may be mentioned as more preferred cyclic multidentate ligands.

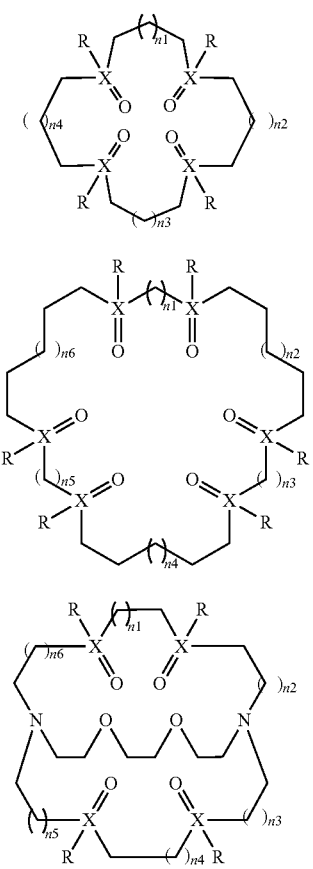

wherein X and R are as defined above; and n1 to n6 each are an integer of 0 (zero) or more, preferably 1 to 5, more preferably 1 to 3, most preferably 1.

The ligand is selected depending upon the type of the rare earth atom as the central atom of the fluorescent complex. The molecular weight of the ligand is generally not more than 2000, preferably not more than 1000. The effect of shielding central rare earth ions can also be enhanced by using dendrimer or the like as the ligand in the fluorescent complex. Since, however, the molecular weight of the dendrimer reaches several thousands, in many cases, an effective fluorescent layer cannot be provided due to the macrostructure of the dendrimer.

The plurality of cyclic multidentate ligands may, if necessary, be mutually bonded. That is, the cyclic multidentate ligands may be linked to each other through a molecular chain to form a dimer, a trimer or a polymer. Specifically, the cyclic multidentate ligands may be bonded to each other, for example, through an alkylene, an ether bond, or an ester bond extended from R or Y in the above general formulae.

The cyclic multidentate ligands represented by formulae (A1) to (A3) can combine with a Lewis acidic rare earth ion to form a coordination bond, because the oxygen atom in X=O is Lewis-basic.

When the cyclic multidentate ligand is coordinated to the rare earth atom, a structure comprising the rare earth atom surrounded by the ring is formed. In this case, preferably the center of the rare earth atom does not conform with the face constituted by the plurality of coordinating groups. When the number of coordinating groups in the cyclic multidentate ligands is 4 or more, due to the structure (conformation) of the cyclic multidentate ligand, all the coordinating groups are not always located on a single plane. The structure, however, is preferably such that the rare earth atom is protruded from the ligand plane determined from the center of gravity of the position of the coordinating groups. In other words, preferably, the ligands are not present in positions symmetrical with respect to the center of the rare earth atom. This structure is likely to be formed when the space defined by the ligands is small, that is, when the ring constituted by the ligands is small. Accordingly, preferably, the ring of the cyclic multidendate ligand is not excessively large.

Since the fluorescent complex used in the present invention has the above structure, asymmetry occurs in the ligand field. This increases the absorption efficiency of the fluorescent complex, resulting in high luminescence efficiency.

This luminescence efficiency is likely to be increased by coordinating a combination of a plurality of types of ligands to the rare earth atom. For example, two or more types of cyclic multidentate ligands having the above structures may be combined, or alternatively the cyclic multidentate ligand having the above structure may be combined with other ligand(s) which has a different structure from said cyclic multidentate ligand. Any conventional coordination compound may be used as the ligand different from the cyclic multidentate ligand having the above structure, and examples thereof include phosphine oxide compounds, carbonyl compounds, pyridine compounds, sulfoxide compounds, and sulfone compounds. A combination of such ligands is likely to improve the solubility or dispersibility of the fluorescent complex in resins or the like, or to increase the luminescence efficiency as a result of asymmetrization of the ligand field.

The cyclic multidentate ligand may be prepared by any desired method. For example, the cyclic multidentate ligand may be prepared by oxidizing a phosphorus atom (trivalent) in heterocrown by a method used in the oxidation of phosphine. The method described, for example, in Journal of the Chemical Society, Abstract, 4685-7, 1956 or Journal of Organic Chemistry, 30(1), 101-5, 1965 may be used in the oxidation reaction. Further, the cyclic multidentate ligand may also be prepared by a cyclization reaction as described in Tetrahedron 1991, V47(3) p 403-10.

The fluorescent complex according to the embodiment comprises the above ligand coordinated to a rare earth atom. The rare earth atom may be properly selected. Europium is particularly preferred from the viewpoints of luminescence efficiency and red color rendering properties. The fluorescent complex according to the embodiment may be prepared by reacting a salt, for example, a chloride, a nitrate, or a hydroxide, containing the rare earth atom with the ligand in a solvent optionally with heating. Solvents which may generally be used herein include water, alcohols, and ester solvents.

The fluorescent complex according to the embodiment has such a property that absorbs light and emits light with a longer wavelength than the absorbed light. When this property is utilized, a combination of the fluorescent complex with a light emitting element, which emits light by taking advantage of electric energy or the like can produce light with a wavelength different from that in the light emitting element. Further, a combination of the fluorescent complex, for example, with a YAG fluorescent substance or coloring matter can realize a light emitting element having excellent color rendering properties.

FIG. 1 is a cross-sectional view of one embodiment of this light emitting element. A fluorescent layer 3 formed of a fluorescent complex according to the embodiment dispersed, for example, in a fluororesin is disposed on an LED chip 2 (generally a plurality of chips) provided on a substrate 1. The fluorescent layer 3 can be formed on the LED chip directly, or above the LED chip, for example, on a resin layer formed on the LED chip. If necessary, a reflecting layer 5 may also be provided. The LED chip 2 emits light upon supply with electric energy through an electrode 4 provided on the substrate 1. The fluorescent complex absorbs light radiated from the LED chip and emits light with a wavelength different from that of absorbed light. Thus, light emitted from the LED chip and light emitted from the fluorescent complex are radiated from the luminescent element. Further, a combination of the fluorescent layer with other fluorescent substrate can vary color rendering properties of the radiated light.

In the above light emitting element, a fluororesin is preferably used as the resin for constituting the fluorescent layer, because the amount of C—H bond and O—H bond contained in the resin is small. Accordingly, a resin having a high percentage fluorination is more preferred. The resin, however, may be properly selected depending upon conditions such as solubility or dispersibility of the fluorescent complex or other components used. Resins usable herein include Cefral Coat FG700X, Cefral Coat A402B, and Cefral Coat A610X manufactured by Central Glass Co., Ltd., LUMIFLON manufactured by Asahi Glass Co., Ltd., ZEONOR manufactured by Zeon Corporation, KYNAR and KYNAR FLEX, manufactured by ATOFINA Japan, Duflon manufactured by Nippon Paint Co., Ltd., and Dyneon THV 220, THV 310 and THV 415 manufactured by Sumitomo 3M Ltd. In addition to the fluorescent complex according to the embodiment, for example, YAG fluorescent substances, alkaline earth metal silicate fluorescent substances, alkaline earth metal phosphate fluorescent substances, halophosphate fluorescent substances, BAM:Eu, Mn, BAM:Eu, ZnS, $SrGa_2S_4$:Eu, oxynitride:Eu, SrAlO4:Eu, alkaline earth apatite:Eu, Ca apatite:Eu, Mn, CaS:Ce, $Y_2SiO_5$:Tb, $Sr_2P_2O_7$:Eu, Mn, and $SrAl_2O_4$:Eu may also be used in the fluorescent layer. Further, white luminescence can also be realized by combining some of them.

Figure 2:
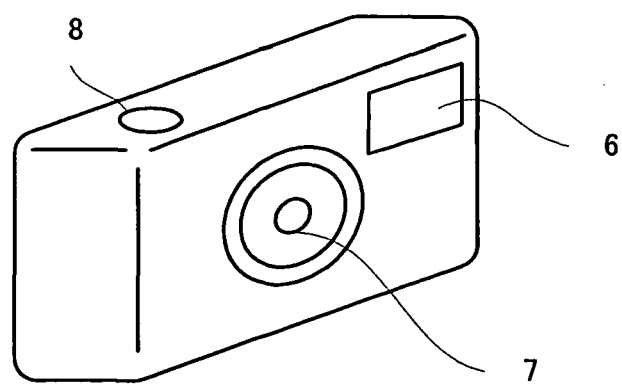
FIG. 2 is a conceptual view of a camera with a flashlight device using the fluorescent complex according to one embodiment.
Figure 3:
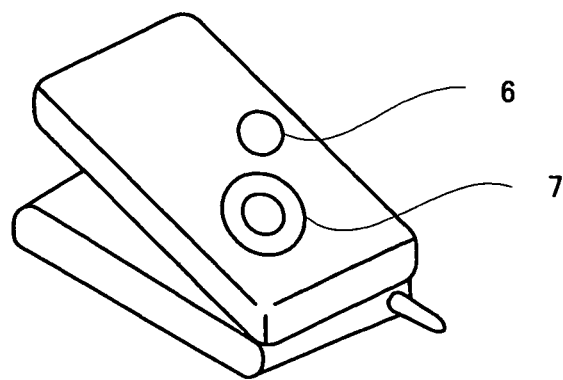
FIG. 3 is a conceptual view of a cellular phone with a camera comprising a flashlight device using the fluorescent complex according to one embodiment.

The above light emitting element as such may be used in a lighting system and further may be applied to a flashlight device utilizing a short luminescence life. In particular, the light emitting element according to the embodiment utilizes elements having small electric energy consumption such as LEDs and thus is useful as a flashlight device for cellular phones with a camera. In such applications, the flashlight device can be used in the same manner as in other conventional light emitting elements. FIGS. 2 and 3 are conceptual diagrams of a camera and a cellular phone with a camera comprising a light emitting element using the fluorescent complex according to one embodiment of the present invention as a flashlight device.

The camera and the cellular phone with a camera each comprise a flashlight device 6, a lens 7, and a shutter button 8 (not shown in FIG. 3). The construction of the camera and the cellular phone with a camera is the same as that of the conventional camera and cellular phone with a camera, except that the light emitting element according to one embodiment of the present invention is used as the flashlight device 6. The light emitting element according to embodiment possesses excellent color rendering properties and long service life and thus is suitable for use in these camera and cellular phone with a camera.

Figure 4:
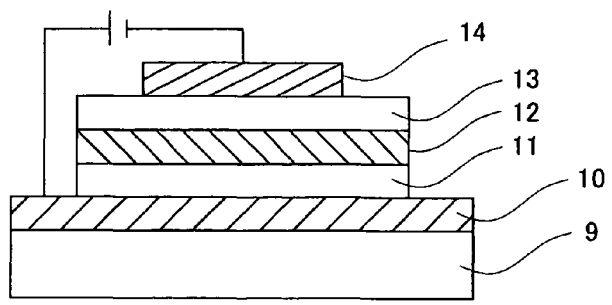
FIGS. 4 to 6 are cross-sectional view of electroluminescent elements according to the embodiments.

Furthermore, the fluorescent complex according to one embodiment of the present invention can also be used in an electroluminescent element. For Example, FIG. 4 shows the cross-sectional view of such an electroluminescent element. The element comprises a glass substrate 9, a cathode 10, a luminescent layer 11, a hole blocking layer 12, an electron transport layer 13, and an anode 14.

A material for the cathode 10 may comprise gold, copper iodide, tin oxide, or indium tin oxide (ITO).

A material for the anode 14 may be a metal which belongs to Group I or II in the periodic table such as sodium, lithium, magnesium, or calcium, or a metal which belongs to Group III in the periodic table such as gallium or indium.

The luminescent layer 11 comprises a host material doped with a guest material. The host material may be, for example, a derivative of aryl amine, a derivative of carbazole, a thiophene origomer or polymer, $Alq_3$ as an Al oxine complex, a perylene compound, a naphthalene compound, a coumarin compound, an oxadiazole compound, an aldazine compound, a bisbenzoxiazorine compound, a bisstyryl compound, pyradine compound, a CPD compound, an In oxine complex, a Zn complex, a Fe oxine complex, or a Ga imine complex. In the electroluminescent element according to one embodiment of the present invention, the host material is doped with the fluorescent complex as the guest material. The fluorescent complex is doped in the host material, for example, by a vacuum deposition method in which the deposition speeds ratio between the host material and the guest material is controlled, or by spin coating a solution which is produced by dissolving a mixture of the host material and the guest material in a solvent.

A material for the hole blocking layer 12 is selected from materials which have large ionization potential and low hole mobility. Examples of the material for the hole blocking layer may be triazole compound and the derivatives thereof.

A material for the electron transport layer 13 may be a metal chelate including $Alq_3$, a multi-ring condensed hydrocarbon, benzoxazole, benzothiazole, tris(8-hydroxyquinolinol) bismuth, or a perylene compound.

EXAMPLES

Although the following Examples further illustrate the present invention, the present invention is not restricted by these Examples.

Synthesis Example

A cyclic compound represented by formula (1) was synthesized by the method described in Tetrahedron 1991, V47 (3) p 403-10. Specifically, the cyclic compound represented by formula (1) was

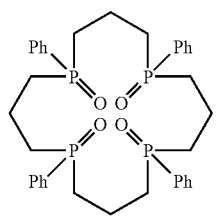

(1)

synthesized by allowing phosphine dioxide bromide (Br(CH$_2$)$_3$P(O)Ph(CH$_2$)$_3$P(O)Ph(CH$_2$)$_3$Br) and 1,3-bis(diphenylphosphino)propane to act on each other.

Example 1

The cyclic compound represented by formula (1) was allowed to act on EuCl$_3$ in the presence of a base in an ethanol solution for coordination. Triphenylphosphine oxide and trioctylphosphine oxide were added thereto each in an amount of 1 molar equivalent based on EuCl$_3$, the mixture was heated with stirring for 2 hr, and the solvent was then removed.

20% by weight of the solid thus obtained and a YAG fluorescent substance were dispersed in a fluoropolymer "Cefral FG700X" which is a fluororesin manufactured by Central Chemical Co., Ltd. An experimental LED flashlight device shown in FIG. 1 was prepared by providing the dispersed fluorescent layer type 2 and providing a fluorescent layer on a chip with a maximum wavelength of 460 nm. For this lighting system, the luminous intensity and general color rendering index were measured under rated drive conditions of 20 mA and 3.4 V per chip (number of chips: 4) and were found to be 6.0 cd and 85, respectively.

Example 2

An LED flashlight device was prepared in quite the same manner as in Example 1, except that a ligand shown in formula (2) was used.

The lighting system thus prepared had a luminous intensity of 5.0 cd and a general color rendering index of 80.

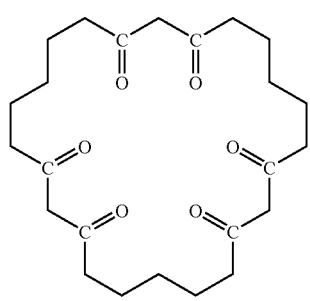

(2)

Example 3

An LED flashlight device was prepared in quite the same manner as in Example 1, except that a ligand shown in formula (3) was used.

The lighting system thus prepared had a luminous intensity of 5.5 cd and a general color rendering index of 85.

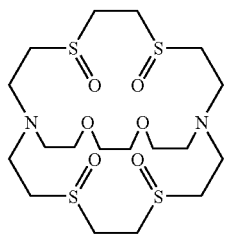

(3)

Comparative Example 1

An experimental LED flashlight device shown in FIG. 1 was prepared in which a fluorescent layer was formed in such a manner that a rare earth complex represented by formula (4) was used in the same molar concentration of europium ions as in Example 1.

The lighting system thus prepared had a luminous intensity of 3.0

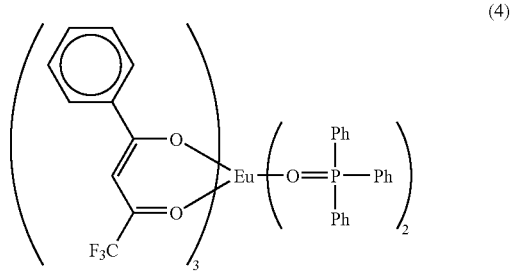

(4)

cd and a general color rendering index of 60. The solubility or dispersibility of the europium complex represented by formula (4) in the resin was unsatisfactory, and, consequently, light scattering occurred in the fluorescent layer. Further, due to vibrational deactivation caused by residual OH in the fluroresin Cefral, the luminous intensity was small, and luminescence of red was weak. Consequently, the general color rendering index appeared to be small.

Example 4

An fluorescent complex represented by formula (5) was synthesized by the method described above.

Indium tin oxide (ITO) was deposited to 200 nm on a glass substrate by sputtering, and then the glass substrate was washed with acetone and 2-propanol sequentially. A light emitting material, as the host material, represented by formula (6) and the fluorescent complex (5) as the guest material were then deposited to 50 nm. on the glass substrate, by a vacuum deposition method in which the deposition speed ratio of the host material to the guest material was 5:1. A triazole compound represented by formula (7) was deposited to 15 nm as the hole blocking layer on the glass substrate, and Alq$_3$ having the thickness of 30 nm layer as electron transport layer and a magnesium layer having the thickness of 150 nm as the anode were deposited on the glass substrate sequentially to prepare an electroluminescent element shown in FIG. 4. The initial brightness was more than 120 cd/m$^2$ when 12 V was applied to the electroluminescent element. Furthermore, no degradation of the brightness was observed after continuous current application of 15 V/300 hours.

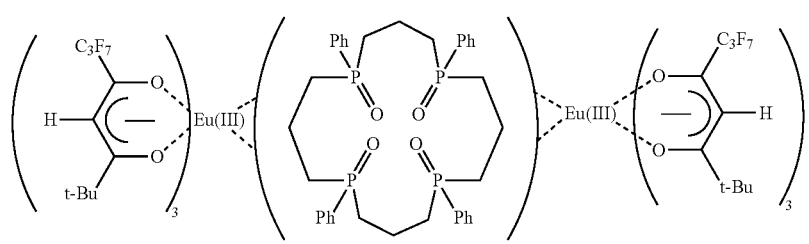

(5)

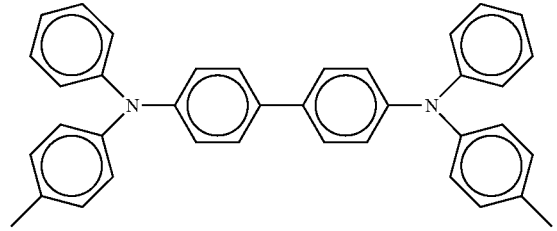

(6)

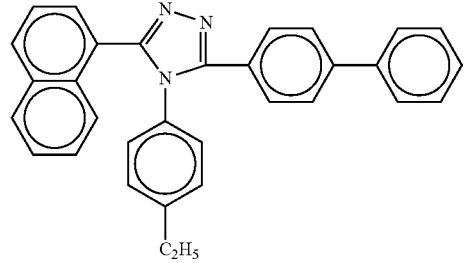

(7)

Comparative Example 2

An electroluminescent element was prepared by same manner as Example 4, except that the compound represented by formula (8) was used as the guest material. The initial brightness is 100 cd/m$^2$ or less when 12 V was applied to the electroluminescent element. Furthermore, 30% of degradation of the brightness was observed after continuous current application of 15 V/300 hours.

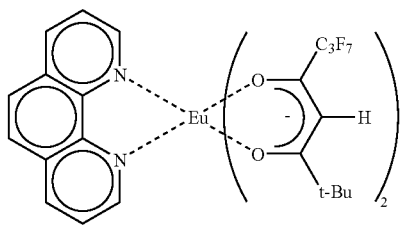

(8)

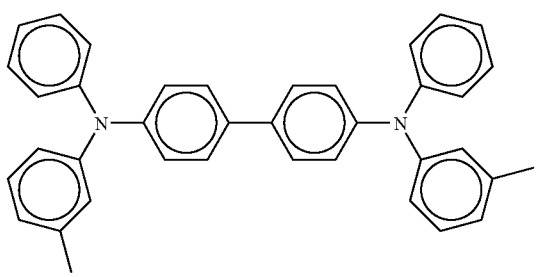

(9)

Example 5

Figure 5:
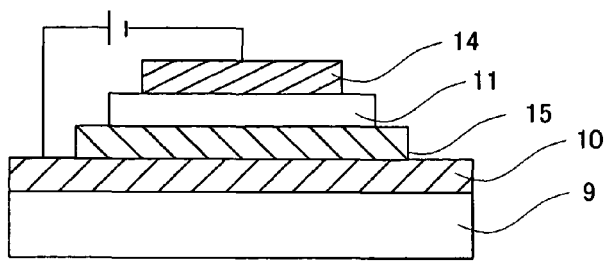

Indium tin oxide (ITO) was deposited to 200 nm on a glass substrate 9 as a cathode 10 by sputtering, then the glass substrate was washed with acetone and 2-propanol sequentially. A light emitting material represented by formula (9) was deposited to 60 nm on the glass substrate as a hole transport layer 15 by a vacuum deposition method, and thus a fluorescent complex represented by formula (5) was deposited to 60 nm on the light emitting material layer 11 as a fluorescent layer, and then Al-Li layer was deposited to 200 nm as anode 14 to prepare an electroluminescent element shown in FIG. 5. The initial brightness is more than 130 cd/m$^2$ when 12 V was applied to the electroluminescent element. Furthermore, no degradation of the brightness was observed after continuous current application of 15 V/300 hours.

Example 6

Figure 6:
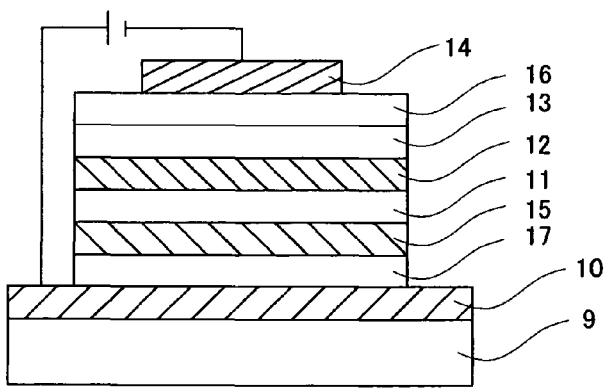

An experimental electroluminescent element shown in FIG. 6 was prepared. Al for the anode 14, Li$_2$O as an electron injection layer 16, Alq3 as an electron transport layer 13, a compound represented by formula (12) as a hole blocking layer 12, a co-evaporation film as a light emitting layer 11, a compound represented by formula 14 as a hole transport layer 15, copper phthalocyanine as hole injection layer 17 and Indium tin oxide were used. The light emitting layer 11 was a co-evaporation film of a compound (10) and a compound (5) as red light emitting layer, a co-evaporation film of a compound (10) and a compound (11) as green light emitting layer, or a co-evaporation film of a compound (10) and a compound (13) as blue light emitting layer, respectively. The initial brightness are more than 150 cd/m$^2$ when 12 V was applied to the each electroluminescent elements. Furthermore, no degradation of the brightness was observed after continuous current application of 15 V/300 hours.

(10)
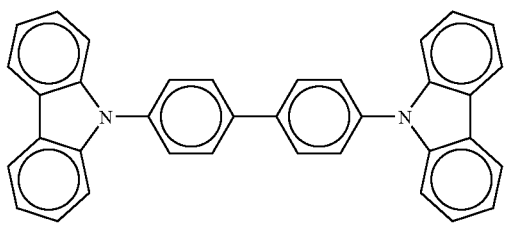

(11)
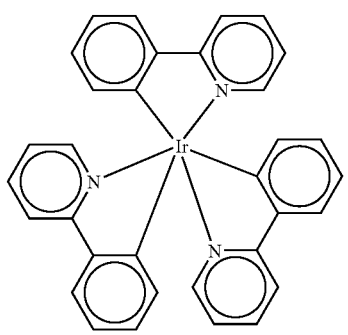

(12)
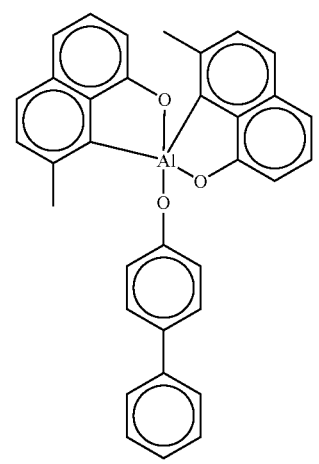

(13)
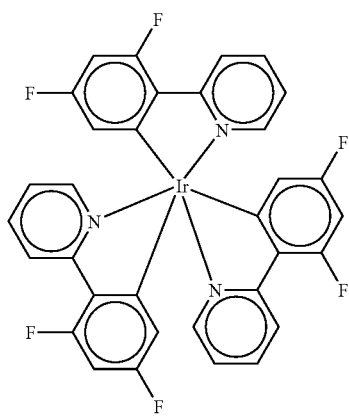

-continued

(14)
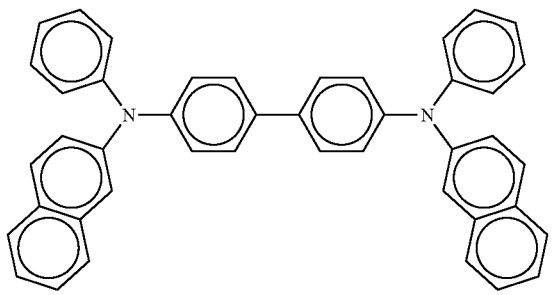

Example 7

Figure 7:
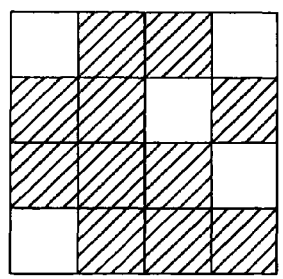
FIG. 7 is a dotted pattern according to the embodiment.

A fluorescent ink was prepared by dissolving a compound represented by formula (5) in fluorinated polymer (Cefral Coat :produced by Central Glass Co. Ltd) wherein the concentration was 10 wt %. Then, the dotted pattern shown in FIG. 7 was printed on a substrate with the fluorescent ink. When the strong light emitting pattern was observed when the pattern was exposed to UV light, although it was not visible under room light.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A fluorescent complex comprising a rare earth atom and at least one ligand having a structure represented by the following formula (A1):

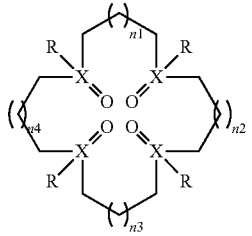

(A1)

wherein
X represents a phosphorous atom,
R represents a group selected from the group consisting of a substituted or unsubstituted straight chain or branched alkyl or alkoxy having 20 or less carbon atoms, phenyl, biphenyl, and naphtyl, each R group can be the same or different, and
n1 to n4 are independently an integer selected from 0-5.

2. The fluorescent complex according to claim 1, wherein said complex comprises plurality of ligands having a structure represented by the formula (A1) and said ligands are mutually bonded.

3. The fluorescent complex according to claim 1, wherein said rare earth atom is a europium atom.

4. A electroluminescent element comprising a cathode, an organic light emitting layer, and anode, wherein the organic light emitting layer comprising the fluorescent complex according to claim 1.

5. A lighting system comprising a light emitting element having a light emitting face and a fluorescent layer disposed on or above said light emitting element on the side of the light emitting faces, said fluorescent layer comprising the fluorescent complex according to claim 1.

6. A camera comprising as a flashlight device a lighting system comprising a light emitting element having a light emitting face and a fluorescent layer disposed on or above said light emitting element on the side of the light emitting face, said fluorescent layer comprising the fluorescent complex according to claim 1.

7. A cellular phone with a camera, the camera comprising as a flashlight device a lighting system comprising a light emitting having a light emitting face element and a fluorescent layer disposed on or above said light emitting element on the side of the light emitting face, said fluorescent layer comprising the fluorescent complex according to claim 1.

* * * * *